(12) United States Patent
Woo et al.

(10) Patent No.: US 9,794,521 B2
(45) Date of Patent: Oct. 17, 2017

(54) APPARATUS AND METHOD OF RESAMPLING EVENT DATA FOR QUANTITATIVE IMPROVEMENT OF PET IMAGE

(71) Applicant: KOREA INSTITUTE OF RADIOLOGICAL & MEDICAL SCIENCES, Seoul (KR)

(72) Inventors: Sang Keun Woo, Seoul (KR); Kyeong Min Kim, Seoul (KR); Tae Won Nam, Seoul (KR); Ji Min Kim, Seoul (KR); Sang Moo Lim, Seoul (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 518 days.

(21) Appl. No.: 14/578,977

(22) Filed: Dec. 22, 2014

(65) Prior Publication Data

US 2015/0186424 A1 Jul. 2, 2015

(30) Foreign Application Priority Data

Dec. 30, 2013 (KR) .................. 10-2013-0167622

(51) Int. Cl.
*H04N 7/18* (2006.01)
*G06F 19/00* (2011.01)
*H04N 1/32* (2006.01)
*G06T 11/00* (2006.01)

(52) U.S. Cl.
CPC ............ *H04N 7/18* (2013.01); *G06F 19/321* (2013.01); *G06T 11/005* (2013.01); *H04N 1/32128* (2013.01)

(58) Field of Classification Search
CPC .... H04N 7/18; H04N 1/32128; G06T 11/005; G06F 19/321
USPC ........................................... 348/77
See application file for complete search history.

(56) References Cited

U.S. PATENT DOCUMENTS

2007/0242798 A1* 10/2007 Popescu .................. A61B 6/56
378/21

OTHER PUBLICATIONS

Woo, et al. "List-event Data Resampling for Quantitative Improvement of PET Image," *Progress in Medical Physics*, vol. 23, No. 4 (2012), pp. 309-316.

* cited by examiner

*Primary Examiner* — Nguyen Truong
(74) *Attorney, Agent, or Firm* — Klarquist Sparkman, LLP

(57) ABSTRACT

Provided are apparatuses and methods of resampling event data for quantitative improvement of a PET image, which acquire a quantitatively-improved new PET image by analyzing a storage format of list data prior to conversion into the PET image and nonparametrically resampling event data from the list data based on the analysis results to improve noise and statistical characteristics thereof. The quantitatively improved new PET image may be acquired by analyzing a storage format of list data constituting the PET image and nonparametrically resampling event data to improve noise and statistical characteristics thereof.

18 Claims, 5 Drawing Sheets

| 43..40 | PACKET TYPE |
|---|---|
| x0 to x7 | Coincidence Event |
| x8 | Single Event |
| x9 | Undefined |
| xA | Counter Tag (Time Mark, single, etc.) |
| xB | Undefined |
| xC | IOS Board Tags (Axis position, gating, etc.) |
| xD | Undefined |
| xE | Extended Packets (Pass-Through, Double, Bulk) |
| xF | Microcontroller Tags |

| DECIMAL NUMBER | BINARY NUMBER | GRAY CODE |
|---|---|---|
| 0 | 0000 | 0000 |
| 1 | 0001 | 0001 |
| 2 | 0010 | 0011 |
| 3 | 0011 | 0010 |
| 4 | 0100 | 0110 |
| 5 | 0101 | 0111 |

FIG. 5

| | |
|---|---|
| 0 0010 1010 | 3 |
| 0 1101 100 | 4 |
| 0 1110 100 | 5 |
| 0 1010 100 | 6 |
| 0 1000 111 | 7 |
| 0 0000 111 | 0 |
| 0 0010 100 | 1 |
| 0 0110 001 | 2 |
| 0 0100 110 | 3 |
| 0 1100 111 | 4 |
| 0 1110 111 | 5 |
| 0 1011 100 | 6 |
| 0 1001 100 | 7 |
| 0 0001 100 | 0 |
| 0 0010 111 | 1 |
| 0 0110 100 | 2 |
| 0 0100 100 | |
| 0 1100 100 | |
| 0 1111 010 | |

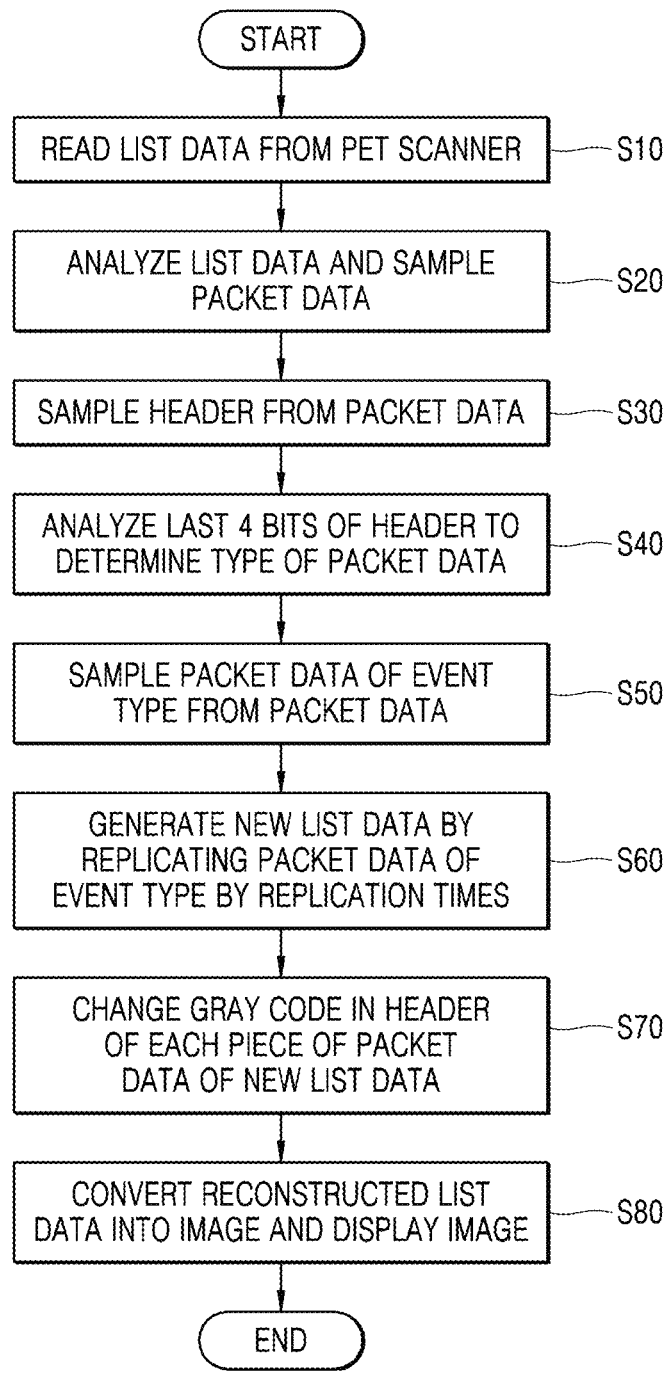

APPARATUS AND METHOD OF RESAMPLING EVENT DATA FOR QUANTITATIVE IMPROVEMENT OF PET IMAGE

RELATED APPLICATION

This application claims the benefit of Korean Patent Application No. 10-2013-0167622, filed on Dec. 30, 2013, in the Korean Intellectual Property Office, the disclosure of which is incorporated herein in its entirety by reference.

BACKGROUND

1. Field

One or more exemplary embodiments relate to apparatuses and methods of resampling event data for quantitative improvement of a positron emission tomography (PET) image, and more particularly, to apparatuses and methods of resampling event data for quantitative improvement of a PET image, which acquires a quantitatively-improved new PET image by analyzing a storage format of list data prior to conversion into the PET image and nonparametrically resampling event data from the list data based on the analysis results in order to improve noise and statistical characteristics thereof.

2. Description of the Related Art

Nuclear medicine imaging and magnetic resonance imaging (MRI) have been complementarily used for focus detection and disease diagnosis, and recently, analysis methods using new data and merged image processing and multi-modal imaging have been developed due to an environmental change such as integration of diagnosis and treatment fields using positron emission tomography (PET) and diffusion weighted-MRI (DW-MRI).

Despite the integration of hardware, multimodal imaging degrades a matching rate due to a lack of a count rate and a mismatch between images due to a difference between acquisition methods of machines. An algorithm for matching between multimodal images intends to remove a mismatch between images by improving a matching rate by using a gradient difference (GD) based on a derivative, a Kullback Leibler distance (KLD) for measurement of the entropy of a discrete probability distribution, and normalized mutual information (NMI) based on information and entropy of an image. Also, a data resampling technique is used to increase a count rate to improve a matching rate between a nuclear medicine image and a DW-MRI image.

In a diagnostic MRI field, Cohen-Adad et al. have introduced a method that rearranges high angular resolution diffusion imaging (HARDI) data by jackknife sampling and regular bootstrap in order to evaluate the quality of HARDI based on Q-Ball imaging (QBI) reconstruction, measures an orientation distribution function (ODF) in each piece of bootstrap data, and performs evaluation based on a change in a b-value determining an echo time and a diffusion degree of tissue.

In a gated MRI image, in order to improve image quality, an EPI image has been acquired based on the existence and nonexistence of heart gating, and the uncertainty of a diffusion tensor image (DTI) with derived parameters has been measured and quantized by residual bootstrap.

In gated PET data, image quality is degraded due to a low count rate and a disease detection capability is degraded due to increased noise, which obstructs quantitative improvement. Also, the low sensitivity of single-photon emission computed tomography (SPECT) data amplifies noise; however, when a filtering technique is used to remove such noise, resolution is degraded. The image quality may be improved when a bootstrap data resampling technique is used in order to overcome this problem.

Huang et al. have intended to improve a diagnosis performance by performing a bootstrap based on sinogram data in whole-body PET imaging to identify a portion influenced by motion and evaluate noise. Buvat has presented a protocol that may improve the quality of PET/SPECT images by using a nonparametric bootstrap method in order to measure the statistical characteristics of a reconstruction algorithm and projection data. Kukreja and Gunn have introduced that a bootstrap method for estimating a parameter error in dynamic PET data may calculate a parameter error based on a parametric image or a region or interest (ROI).

Groiselle and Glick have introduced a method that performs a simulation by constructing 20 data sets by using a bootstrap technique in order to evaluate noise in 3D OSEM list-mode iterative reconstruction, and evaluates noise by sampling an event of a list data set having the same size.

A bootstrap method for reducing count rate degradation in the acquisition of a nuclear medicine image and an MRI image is difficult to use in clinical stages due to a lot of data processing. However, since efforts have recently been made to use the bootstrap method in the clinical stages, due to an improvement in computer performance and an improvement in algorithms, a technology implementing the bootstrap method is required.

SUMMARY

One or more exemplary embodiments include apparatuses and methods of resampling event data for quantitative improvement of a PET image, which may acquire a quantitatively-improved new PET image by analyzing a storage format of list data constituting the PET image and nonparametrically resampling event data from the list data based on the analysis results in order to improve noise and statistical characteristics thereof.

Additional aspects will be set forth in part in the description which follows and, in part, will be apparent from the description, or may be learned by practice of the presented exemplary embodiments.

According to one or more exemplary embodiments, an apparatus for resampling event data for quantitative improvement of a PET image includes: a data reading unit reading list data from a PET scanner; a packet sampling unit analyzing the read list data on a bit basis and sampling packet data having a length of 48 bits and a first bit of '0'; a header sampling unit sampling the first 8 bits of a header from the sampled packet data; a type classifying unit analyzing the last 4 bits of the sampled header to determine a type of each piece of packet data, and sampling packet data of an event type from the sampled packet data; and a reconstructing unit reconstructing the packet data by increasing a data amount thereof by replicating the sampled packet data of the event type.

The reconstructing unit may include: a replicating unit generating new list data by replicating the sampled packet data of the event type by predetermined replication times; and an order adjusting unit changing a gray code such that a gray code located at second to fourth bits is sequentially repeated in a header of each piece of packet data included in the new list data.

The event type may be one of "Coincidence Event" and "Single Event".

The apparatus may further include an image generating unit generating an image by converting the reconstructed packet data, and displaying the generated image.

According to one or more exemplary embodiments, a method of resampling event data for quantitative improvement of a PET image includes: reading list data from a PET scanner; analyzing the read list data on a bit basis and sampling packet data having a length of 48 bits and a first bit of '0'; sampling the first 8 bits of a header from the sampled packet data; analyzing the last 4 bits of the sampled header to determine a type of each piece of packet data, and sampling packet data of an event type from the sampled packet data; and reconstructing the packet data by increasing a data amount thereof by replicating the sampled packet data of the event type.

According to one or more exemplary embodiments, a non-transitory computer-readable recording medium stores a program that performs the above method when executed by a computer.

BRIEF DESCRIPTION OF THE DRAWINGS

These and/or other aspects will become apparent and more readily appreciated from the following description of the exemplary embodiments, taken in conjunction with the accompanying drawings in which:

FIG. 5 is a diagram illustrating an analysis of a header portion of the packet data;

FIG. 8 is a flowchart of a method of resampling event data for quantitative improvement of a PET image, according to an exemplary embodiment.

DETAILED DESCRIPTION

Figure 1:
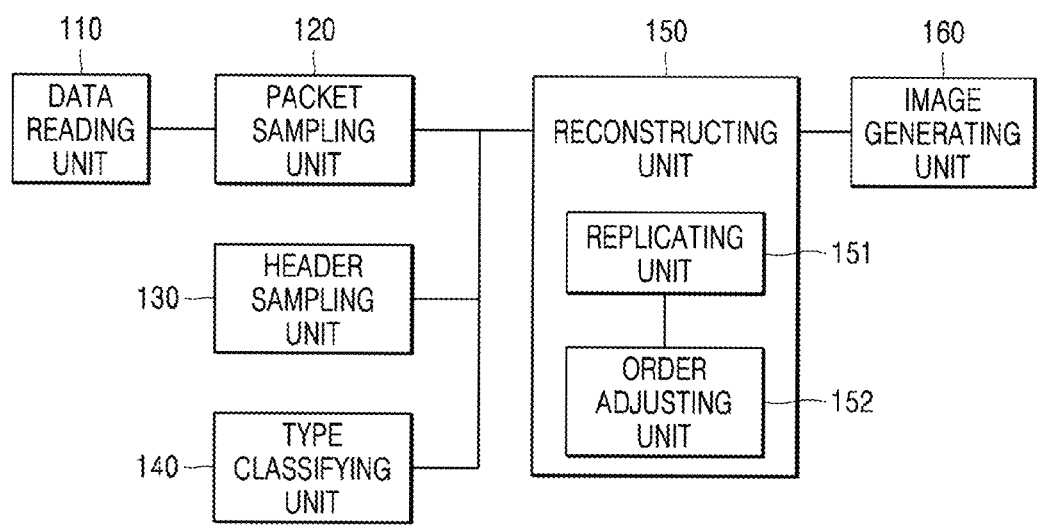
FIG. 1 is a block diagram of an apparatus for resampling event data for quantitative improvement of a PET image, according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

While the inventive concept is susceptible to various modifications and alternative forms, specific embodiments thereof are shown by way of example in the drawings and will herein be described in detail. However, it should be understood that the inventive concept is not limited to the particular forms described and covers all modifications, equivalents, and alternatives falling within the spirit and scope of the inventive concept.

Although terms such as "first" and "second" may be used herein to describe various elements or components, these elements or components should not be limited by these terms. These terms are only used to distinguish one element or component from another element or component. For example, a first element may be termed a second element, and, similarly, a second element may be termed a first element, without departing from the scope of the inventive concept.

The terminology used herein is for the purpose of describing particular embodiments only and is not intended to limit the inventive concept. As used herein, the singular forms "a", "an", and "the" are intended to include the plural forms as well, unless the context clearly indicates otherwise. It will be understood that terms such as "comprise", "include", and "have", when used herein, specify the presence of stated features, integers, steps, operations, elements, components, or combinations thereof, but do not preclude the presence or addition of one or more other features, integers, steps, operations, elements, components, or combinations thereof.

Unless otherwise defined, all terms (including technical and scientific terms) used herein have the same meaning as commonly understood by one of ordinary skill in the art to which the inventive concept belongs.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments will be described in detail with reference to the accompanying drawings. In the drawings, like reference numerals denotes like elements.

FIG. 1 is a block diagram of an apparatus 100 for resampling event data for quantitative improvement of a PET image, according to an exemplary embodiment.

Referring to FIG. 1, the apparatus 100 for resampling event data for quantitative improvement of a PET image, according to an exemplary embodiment may include a data reading unit 110, a packet sampling unit 120, a header sampling unit 130, a type classifying unit 140, and a reconstructing unit 150. The apparatus 100 for resampling event data for quantitative improvement of a PET image may further include an image generating unit 160.

The data reading unit 110 reads list data constituting a PET image. The PET image is generated by converting and compiling the list data, and the list data is raw data prior to conversion into an image. The list data is acquired from a PET scanner.

The packet sampling unit 120 analyzes the list data on a bit basis and samples packet data including 48 bits.

Figure 2:
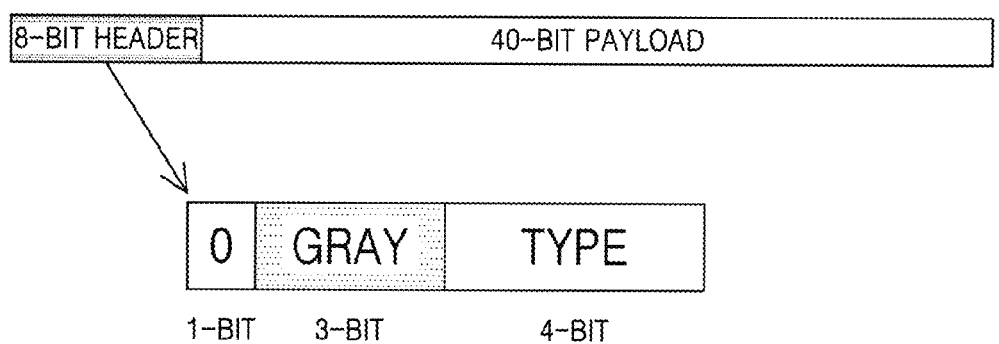
FIG. 2 is a diagram illustrating packet data.

FIG. 2 is a diagram illustrating packet data.

As illustrated in FIG. 2, the packet data constituting the list data has a size of 48 bits and includes an 8-bit header and a 40-bit payload.

The first bit of the 8-bit header is set to '0', the next 3 bits include a gray code, and the remaining 4 bits include type information of the packet data.

Figures 3, 4:
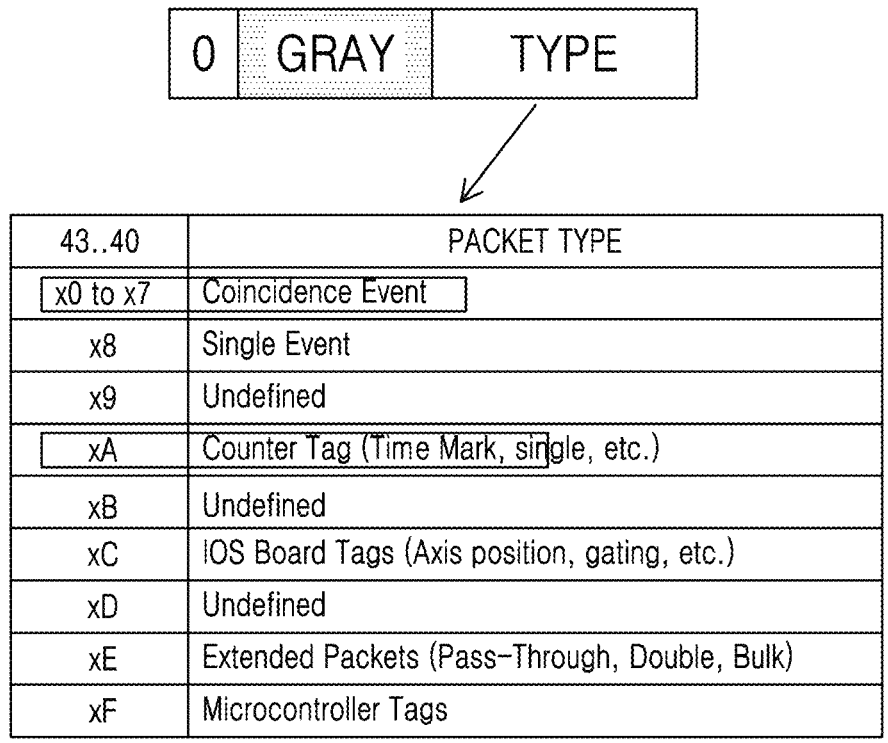
FIG. 3 is a diagram illustrating type information.
FIG. 4 is a diagram illustrating a gray code.

FIG. 3 is a diagram illustrating type information.

Referring to the table of FIG. 3, it may be seen that a number obtained by converting the 4-bit type information into a hexadecimal number corresponds to each type.

When the type information of the packet data corresponds to hexadecimal numbers 'x0' to 'x7', the type of the packet data is "Coincidence Event". When the type information of the packet data is a hexadecimal number 'xA', the type of the packet data is "Counter Tag (Time Mark, Single, etc)".

Since the most important types for sampling of the PET image are "Coincidence Event" and "Single Event", "Coincidence Event" and "Single Event" need to be separately sampled from the list data in order to re-generate an image later.

As described above, the packet sampling unit 120 analyzes the list data on a bit basis and samples the packet data including 48 bits.

Since the list data is information corresponding to a set of binary numbers, it may be cut in various ways. However, as described above, the first bit of the 48-bit packet data is always set to '0'. Thus, when the list data is analyzed, it may be seen that a portion with the first bit having always a value of '0' is continuously repeated at intervals of 48 bits, and it may be seen that a 48-bit data stream with the first bit having a value of '0' is the packet data.

Thus, the packet sampling unit 120 analyzes the list data on a bit basis and samples the packet data from the list data by cutting off the list data such that the initial bit thereof includes '0' when the list data is cut at intervals of 48 bits.

Next, the header sampling unit 130 samples a header from each piece of packet data sampled by the packet sampling unit 120. As illustrated in FIG. 2, since the header is the first 8 bits in the packet data, the header sampling unit 130 may sample the first 8 bits as the header from the packet data.

Thereafter, the type classifying unit 140 classifies a type of each piece packet data by analyzing the last 4 bits in the sampled header and only samples the packet data of an event type including "Coincidence Event" and "Single Event".

As illustrated in FIG. 3, the last 4 bits of the header represent a data type of the packet data. The type classifying unit 140 analyzes the last 4 bits of the header and only samples the packet data corresponding to the event type among the pieces of packet data sampled by the packet sampling unit 120.

The type information of FIG. 3 will be described in more detail.

Among a plurality of types, "Counter Tag", "IOS Board Tags", and "Microcontroller Tags" types are tag types influencing an event. "Counter Tag" and "IOS Board Tags" separately have 4-bit sub type bits after a type bit of each header, and their properties are determined by the 4-bit sub type bits.

"Extended Packets" indicates that "Coincidence Event" and "Single Event" represent more data streams by increasing a limit of having only 48-bit limited data, and "Undefined" represents a type of which content is not opened.

The reconstructing unit 150 replicates the packet data of the event type sampled by the type classifying unit 140 and adjusts an order thereof to generate reconstructed packet data. The reconstructing unit 150 includes a replicating unit 151 and an order adjusting unit 152.

The replicating unit 151 replicates the packet data of the event type sampled by the type classifying unit 140, to increase a data amount of the packet data to be analyzed.

For example, when images are captured by the PET scanner for only 10 minutes, packet data acquired for 10 minutes exists in the list data. The packet data acquired for 10 minutes includes various types of data, including event data. The event data means the packet data corresponding to the event type.

When the event data is replicated to increase an amount by two times and then an image thereof is analyzed, an image capturing time may be increased due to the increased event data and also noise in the image may be reduced. However, since the processing time and noise tend to increase as the data replication amount increases, the data replication amount has to be properly adjusted. Replication times may be determined to be proper times.

When data is replicated, information related to an order is included in a header portion of the packet data. Thus, when compiling is performed for conversion into an image later, the compiling may fail.

In order to solve this problem, after the packet data is replicated by the replicating unit 151, the order adjusting unit 152 adjusts the packet data by changing a gray code of a header in the replicated packet data.

As illustrated in FIG. 2, the gray code is a 3-bit code, which is disposed at the second to fourth bits in the header, and is information that determines an order of each piece of packet data.

FIG. 4 is a diagram illustrating a gray code, and FIG. 5 is a diagram illustrating an analysis of the header portion of the packet data.

The gray code is a code compensating for the problem of a binary number, which is similar but more effective than the binary number. As illustrated in FIG. 4, unlike the binary number, the gray code changes only bit-by-bit.

The gray code is a non-weighted code. Thus, the gray code is unsuitable for an operation, but is mainly used as a code for an input/output device. The gray code becomes a new code when a single bit thereof changes. Thus, when the gray code is used as an input code, an error is reduced. When the gray code is used, an error is reduced, because a change width is small in representing a changing amount.

FIG. 5 is a diagram illustrating an analysis of the header portion of the packet data that is actually sampled. In FIG. 5, when a gray code portion corresponding to a red box in the header is analyzed, it may be seen that the gray code portion continuously changes repeatedly from 0 to 7.

The gray code portion in the packet data is a portion that determines an order of the packet data. Only when the order of the gray code is constantly repeated, compiling of the packet data for image conversion may be successfully performed.

Thus, the order adjusting unit 152 changes each gray code portion such that the gray code portion is sequentially repeated from 0 to 7 in the header of each piece of packet data that is replicated and reconstructed.

The packet data reconstructed by increasing the data amount thereof by the replicating unit 151 and then adjusting the order thereof by the order adjusting unit 152 is provided to the image generating unit 160 for image analysis.

The replicating unit 151 and the order adjusting unit 152 will be described in more detail.

The replicating unit 151 replicates the packet data of the event type to increase the data amount of the packet data to be analyzed. In this case, the replicating may be performed by any one of the following methods:

The first method constructs a population by sampling the packet data of the event type from the previous original list data, randomly samples the packet data of the event type from the constructed population, and combines the randomly-sampled packet data with the previous list data to generate new list data, wherein the new list data is generated by increasing the number of pieces of packet data of the event type by predetermined replication times.

For example, it is assumed that list data acquired for a certain period of time includes 1000 pieces of packet data. In this case, when there are 500 pieces of packet data of the event type among the 1000 pieces of packet data and the predetermined replication times is 10 times, the replicating unit 51 randomly samples 5000 pieces of packet data of the event type from the population including 500 pieces of packet data of the event type, combines the sampled 5000 pieces of packet data of the event type with the previous list data to generate new list data.

Thereafter, the order adjusting unit 152 acquires reconstructed list data by changing each gray code portion such that the gray code portion located at the second to fourth bits is sequentially repeated from 0 to 7 in the header of each piece of packet data included in the new list data.

The second method constructs a population by sampling the packet data of the event type from the previous original list data, increases a data amount thereof by replicating the previous list data by predetermined replication times, and changes each piece of packet data of the event type included in the list data with an increased data amount into the packet data that is randomly sampled from the population, to generate new list data with the number of pieces of packet data of the event type increased by the predetermined replication times.

For example, it is assumed that list data acquired for a certain period of time includes 1000 pieces of packet data. In this case, when there are 500 pieces of packet data of the event type among the 1000 pieces of packet data and the predetermined replication times is 10 times, the replicating unit 51 replicates the 1000 pieces of packet data by 10 times to acquire list data including 10000 pieces of packet data.

Thereafter, the replicating unit 151 generates new list data by changing the packet data of the event type in the list data including the 10000 pieces of packet data into the packet data of the event type that is randomly sampled from a population. Herein, the population is 500 pieces of packet data classified as the event type in the previous list data.

In this case, without changing the previous list data portion, the replicating unit 151 may change only the list data portion that is newly added by replication.

Thereafter, the order adjusting unit 152 acquires reconstructed list data by changing each gray code portion such that the gray code portion is sequentially repeated from 0 to 7 in the header of each piece of packet data constituting the new list data.

Figure 6:
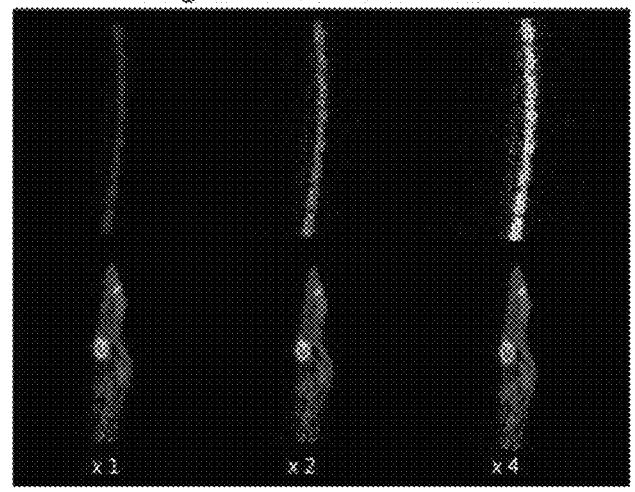
FIGS. 6 and 7 are images analyzed after the packet data is increased.
Figure 7:
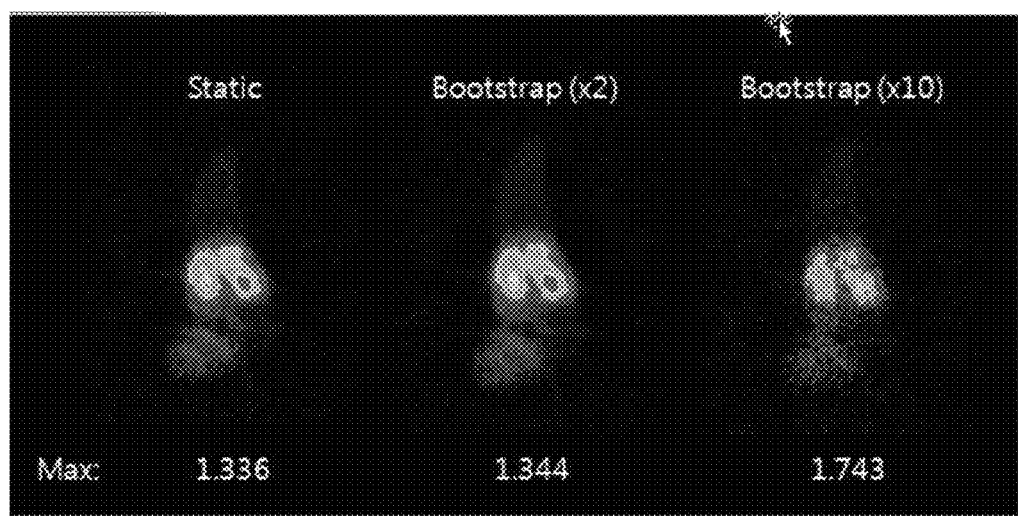

FIGS. 6 and 7 are images analyzed after the packet data is increased by two times and four times, respectively.

Referring to FIG. 6, it may be seen that an image becomes vague as a replication amount increases with the increase of noise due to the increase of a packet data amount.

In order to compensate for a lack of the count rate of PET event data, an image change due to an artificial event type data increase was evaluated as illustrated in FIG. 7. In FIG. 7, a left image is an image reconstructed by using the original list data, a center image is an image reconstructed by increasing the event type packet data by two times with respect to a time mark, and a right image is an image reconstructed by increasing the event type packet data by 10 times.

A count rate of the image reconstructed by using the event increased by 2 times was increased to 1.344 in comparison with a count rate 1.336 of the original, noise was reduced, and contrast was improved.

The right image is an image reconstructed by using the packet data increased by 10 times in comparison with the original, and it may be seen that the count rate of the image with an event increased by 10 times was improved to 1.743 but noise was also increased accordingly.

When data of a certain time domain is expanded or artificially increased with respect to each piece of packet data, the rate of noise may be increased on the contrary as illustrated in FIGS. 6 and 7. Thus, count improvement by an event increase using a nonparametric resampling method has to be performed without a reduction of a signal-to-noise ratio (SNR) in consideration of the data sampling and data expansion range.

A general acquisition time in PET image acquisition is 10 minutes. 17 minutes was taken when 440-Mbyte data generated in F18 10-minute data acquisition was nonparametrically sampled by a central processing unit (CPU). Thus, when sampling times is increased to 100 times in order to reduce noise and improve an SNR, a performance time of 1,700 minutes is required. When performed by 500 times, sampling has to be performed for 8,500 minutes (i.e., 6 days). Thus, in order to reduce the performance time, data processing has to be performed by a graphics processing unit (GPU) instead of by a CPU. Also, a change in spatial resolution has to be quantitatively evaluated by a phantom experiment.

In the multimodal imaging technology of PET and MRI, the development of an integrated scanner and research on an analysis method are actively performed for performance improvement in the diagnosis and treatment response evaluation. However, a gated merged image based on a biometric signal is required in a region influenced by motion. As for a gated PET image, noise increases due to a decrease in count rate. As for a gated DW-MRI image for reduction of the uncertainty of a b value, repeated performance is difficult due to an increase in acquisition time.

Thus, in comparison with the conventional method, image improvement by the increase of acquired data reduces a multimodal image acquisition time and improves a matching rate between multimodal images, thereby improving a tumor evaluation performance by providing evaluation data of the same ROI. Thus, this research will be used in the heart and tumor treatment response evaluation, which is actively-performed in a preclinical stage due to the establishment of quantitatively-improved multimodal image acquisition technology, to increase clinical applicability and assist in new drug development, and will become base technology that may apply new nuclear medicine image-based merged image processing and analysis technology to clinical fields.

A method of resampling event data for quantitative improvement of a PET image, according to an exemplary embodiment, will be described below. Since the method of resampling event data for quantitative improvement of a PET image, according to an exemplary embodiment, is performed by and is substantially identical to the apparatus for resampling event data for quantitative improvement of a PET image according to an exemplary embodiment, redundant descriptions thereof will be omitted herein.

FIG. 8 is a flowchart of a method of resampling event data for quantitative improvement of a PET image, according to an exemplary embodiment.

First, the data reading unit 110 of the apparatus 100 for resampling event data for quantitative improvement of a PET image (hereinafter, referred to as the event data resampling apparatus 100) reads list data from a PET scanner (S10).

Thereafter, the packet sampling unit 120 of the event data resampling apparatus 100 analyzes the read list data on a bit basis and samples packet data having a length of 48 bits and a first bit of '0' (S20).

The header sampling unit 130 of the event data resampling apparatus 100 samples a header of the first 8 bits from the sampled packet data (S30).

The type classifying unit 140 of the event data resampling apparatus 100 analyzes the last 4 bits of the sampled header to determine a type of each piece of packet data (S40) and samples packet data of an event type from the sampled packet data (S50).

The reconstructing unit 150 of the event data resampling apparatus 100 reconstructs the packet data by increasing a data amount thereof by replicating the sampled packet data of the event type. The reconstructing of the packet data includes the following two steps:

The replicating unit 151 of the reconstructing unit 150 generates new list data by replicating the sampled packet data of the event type by predetermined replication times (S60).

As described above, the replicating of the sampled packet data may be performed by the following two methods:

The first method constructs a population by sampling the packet data of the event type from the previous original list data, randomly samples the packet data of the event type from the constructed population, and combines the randomly-sampled packet data with the previous list data to generate new list data, wherein the new list data is generated by increasing the number pieces of packet data of the event type by predetermined replication times.

The second method constructs a population by sampling the packet data of the event type from the previous original list data, increases a data amount thereof by replicating the previous list data by predetermined replication times, and changes each piece of packet data of the event type included in the list data with an increased data amount into the packet data that is randomly sampled from the population, to generate new list data with the number of pieces of packet data of the event type that increased by the predetermined replication times.

Thereafter, the order adjusting unit 152 of the reconstructing unit 150 changes the gray code such that the gray code located at the second to fourth bits is sequentially repeated in the header of each piece of packet data included in the new list data (S70).

The image generating unit 160 of the event data resampling apparatus 100 generates an image by converting the reconstructed packet data and displays the generated image (S80).

As described above, according to the one or more of the above exemplary embodiments, a quantitatively-improved new PET image may be acquired by analyzing a storage format of list data constituting a PET image and resampling event data in order to improve noise and statistical characteristics thereof.

Also, according to the one or more of the above exemplary embodiments, in comparison with the conventional method, the image improvement by the data resampling reduces a multimodal image acquisition time and improves a matching rate between multimodal images, thereby improving a tumor evaluation performance by providing evaluation data on the same ROI.

In addition, other exemplary embodiments may also be implemented through computer-readable code/instructions in/on a medium, e.g., a computer-readable medium, to control at least one processing element to implement any above-described exemplary embodiment. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer-readable code is stored/transferred and executed in a distributed fashion. Furthermore, the processing element could include a processor or a computer processor, and processing elements may be distributed and/or included in a single device.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. An apparatus for resampling event data for quantitative improvement of a positron emission tomography (PET) image, the apparatus comprising:
   a data reading unit reading list data from a PET scanner;
   a packet sampling unit analyzing the read list data on a bit basis and sampling packet data having a length of 48 bits and a first bit of '0';
   a header sampling unit sampling the first 8 bits of a header from the sampled packet data;
   a type classifying unit analyzing the last 4 bits of the sampled header to determine a type of each piece of packet data and sampling packet data of an event type from the sampled packet data; and
   a reconstructing unit reconstructing the packet data by increasing a data amount thereof by replicating the sampled packet data of the event type.

2. The apparatus of claim 1, wherein the reconstructing unit comprises:
   a replicating unit generating new list data by replicating the sampled packet data of the event type by predetermined replication times; and
   an order adjusting unit changing a gray code such that the gray code located at second to fourth bits is sequentially repeated in a header of each piece of packet data included in the new list data.

3. The apparatus of claim 1, wherein the event type is one of "Coincidence Event" and "Single Event".

4. The apparatus of claim 2, wherein the replicating unit constructs a population with the sampled packet data of the event type, randomly samples the packet data of the event type from the constructed population, and combines the randomly-sampled packet data with previous list data to generate the new list data, wherein the new list data is generated by increasing the number of pieces of packet data of the event type by predetermined replication times.

5. The apparatus of claim 2, wherein the replicating unit constructs a population with the sampled packet data of the event type, increases a data amount thereof by replicating previous list data by predetermined replication times, and changes each piece of packet data of the event type included in the list data with an increased data amount into the packet data that is randomly sampled from the population, to generate the new list data.

6. The apparatus of claim 1, further comprising an image generating unit generating an image by converting the reconstructed packet data and displaying the generated image.

7. A method of resampling event data for quantitative improvement of a positron emission tomography (PET) image, the method comprising:

reading list data from a PET scanner;

analyzing the read list data on a bit basis and sampling packet data having a length of 48 bits and a first bit of '0';

sampling the first 8 bits of a header from the sampled packet data;

analyzing the last 4 bits of the sampled header to determine a type of each piece of packet data and sampling packet data of an event type from the sampled packet data; and reconstructing the packet data by increasing a data amount thereof by replicating the sampled packet data of the event type.

8. The method of claim 7, wherein the reconstructing of the packet data comprises:

generating new list data by replicating the sampled packet data of the event type by predetermined replication times; and changing a gray code such that the gray code located at second to fourth bits is sequentially repeated in a header of each piece of packet data included in the new list data.

9. The method of claim 7, wherein the event type is one of "Coincidence Event" and "Single Event".

10. The method of claim 8, wherein the generating of the new list data constructs a population with the sampled packet data of the event type, randomly samples the packet data of the event type from the constructed population, and combines the randomly-sampled packet data with previous list data to generate the new list data, wherein the new list data is generated by increasing the number of pieces of packet data of the event type by predetermined replication times.

11. The method of claim 8, wherein the generating of the new list data constructs a population with the sampled packet data of the event type, increases a data amount thereof by replicating previous list data by predetermined replication times, and changes each piece of packet data of the event type included in the list data with an increased data amount into the packet data that is randomly sampled from the population, to generate the new list data.

12. The method of claim 7, further comprising generating an image by converting the reconstructed packet data and displaying the generated image.

13. A non-transitory computer-readable recording medium that stores a program that performs the method of claim 7 when executed by a computer.

14. A non-transitory computer-readable recording medium that stores a program that performs the method of claim 8 when executed by a computer.

15. A non-transitory computer-readable recording medium that stores a program that performs the method of claim 9 when executed by a computer.

16. A non-transitory computer-readable recording medium that stores a program that performs the method of claim 10 when executed by a computer.

17. A non-transitory computer-readable recording medium that stores a program that performs the method of claim 11 when executed by a computer.

18. A non-transitory computer-readable recording medium that stores a program that performs the method of claim 12 when executed by a computer.

* * * * *